United States Patent [19]

McPherson et al.

[11] Patent Number: 5,001,160
[45] Date of Patent: Mar. 19, 1991

[54] 1-ARYL-1-HYDROXY-1-SUBSTITUTED-3-(4-SUBSTITUTED-1-PIPERAZINYL)-2-PROPANONES AND THEIR USE IN TREATMENT OF NEUROGENIC BLADDER DISORDERS

[75] Inventors: Daniel W. McPherson, Oak Ridge, Tenn.; John P. Carter, Baltimore, Md.

[73] Assignee: Marion Laboratories, Inc., Kansas City, Mo.

[21] Appl. No.: 372,009

[22] Filed: Jun. 27, 1989

Related U.S. Application Data

[63] Continuation-in-part of Ser. No. 187,649, Apr. 28, 1988, abandoned.

[51] Int. Cl.⁵ ................... A61K 31/495; C07D 295/04
[52] U.S. Cl. .................................... 514/255; 514/252; 544/60; 544/121; 544/360; 544/372; 544/380; 544/394; 544/399
[58] Field of Search ................. 544/60, 121, 360, 372, 544/380, 394, 399; 514/252, 255

[56]  References Cited

U.S. PATENT DOCUMENTS

| | | | |
|---|---|---|---|
| 3,073,842 | 1/1963 | Schlesinger et al. | 544/397 |
| 3,125,577 | 3/1964 | Biel | 544/399 |
| 3,157,656 | 11/1964 | Krapcho | 544/394 |
| 3,395,146 | 7/1968 | Satzinger | 544/399 |
| 3,873,546 | 3/1975 | Becker et al. | 544/397 |
| 4,476,129 | 10/1984 | Gootjes et al. | 544/397 |

OTHER PUBLICATIONS

Amos E. Light et al., Chem. Abst., vol. 51, 11657d (1957).
Chemical Abstracts, Col., vol. 6, p. 9044s.
Chemical Abstracts, Col., vol. 6, p. 9517s.

*Primary Examiner*—Cecilia Shen
*Attorney, Agent, or Firm*—Theresa M. Gillis

[57]  ABSTRACT

Compounds are disclosed having the formula:

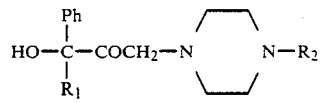

in which
R$_1$ is a C$_1$ to C$_{12}$ alkyl, said alkyl being straight or branched chain, saturated or unsaturated, monosubstituted or unsubstituted, said substituents being selected from piperidine, pyrrolidine, morpholine, thiomorpholine or cycloalkyl of 3 to 7 carbons, a cycloalkyl of 3 to 9 carbons, a lower alkylcycloalkyl of 4 to 9 carbons, or a polycycloalkyl of 2 to 3 rings containing 7 to 12 carbons;
R$_2$ is hydrogen, phenyl, phenyl singly or multiply substituted with halogen, hydroxy, lower alkoxy, methylene dioxy, nitro, lower alkyl or trifluoromethyl, lower alkyl, said alkyl being branched chain or straight, saturated, unsaturated, or cyclic and substituted or unsubstituted, said substituents being selected from thienyl, pyrrolyl, pyridyl, furanyl, hydroxy, lower alkoxy, or acetoxyalkyl wherein the alkyl group has 1 to 3 carbons, phenyl, phenyl substituted with halogen, hydroxy, lower alkoxy, lower alkyl, nitro, methylene dioxy or trifluoromethyl,
Ph is phenyl or phenyl para-substituted by halogen, lower alkyl, lower alkoxy or trifluoromethyl; and the pharmaceutically acceptable nontoxic salts thereof.

Pharmaceutical compositions containing the compounds and methods for the treatment of neurogenic bladder disorders are also disclosed. In the preferred compound Ph is phenyl, R$_1$ is cyclobutyl and R$_2$ is benzyl.

12 Claims, No Drawings

1-ARYL-1-HYDROXY-1-SUBSTITUTED-3-(4-SUBSTITUTED-1-PIPERAZINYL)-2-PROPANONES AND THEIR USE IN TREATMENT OF NEUROGENIC BLADDER DISORDERS

This application is a continuation-in-part of U.S. application Ser. No 07/187,649, filed Apr. 28, 1988 now abandoned.

Background of the Invention

1. (a) Field of Invention

This invention relates to 1-substituted-1-hydroxy-1-aryl-3-(4-substituted-1-piperazinyl)-2-propanones having potent antimuscarinic activity, to pharmaceutical compositions containing such compounds, and to the use of the compounds to treat neurogenic bladder disorder.

2. (b) State of the Art

Neurogenic bladder disease is defined as a disorder involving loss of control of urination. The major symptoms can be urinary frequency, urinary retention or incontinence.

There are two types of lesions that come under the rubric of neurogenic bladder. The first, upper motoneuron lesion, leads to hypertonia and hyperreflexia of the bladder, a spastic condition, giving rise to symptoms of urinary frequency and incontinence. The second lesion, a lower motoneuron lesion, involves hypotonia and hyporeflexia of the bladder, and in more severe conditions, complete distension and atonia of the bladder muscle. Thus, this is a flaccid condition. The major symptoms in this condition are urinary retention, since the voicing reflex has been lost, and incontinence, which occurs when the bladder "leaks", being full to overflowing.

The flaccid or hypotonic bladder is the easier condition to treat. The aim in treatment is to produce a contraction of the bladder, while avoiding contraction of the bladder neck or the urethra. Parasympathomimetic compounds (cholinergic agonists) are commonly employed to stimulate the excitatory muscarinic receptor on the bladder smooth muscle. The most widely used compound in this class is bethanechol, a muscarinic receptor agonist. This is given in combination with the alpha-adrenergic antagonist phenoxybenzamine to prevent sympathetic stimulation of the bladder neck muscle. Bethanechol is also sometimes given in combination with baclofen, a skeletal muscle receptor antagonist. In general, however, urologists and internists have been moving away from pharmacological treatment of the hypotonic bladder, and prefer to institute the physical maneuver of intermittent catheterization.

The majority of neurogenic bladder patients have the spastic or hypertonic condition, which is usually more difficult to treat. In this instance, the usual aim of the clinician is to attempt to convert the condition of hyperreflexia and hypertonia to hypotonia thereby treating the primary problem of incontinence. When the condition has been converted to hypotonia it can be straightforwardly managed by intermittent catheterization. There is a significant population of patients who cannot be converted completely from the hypertonic to the hypotonic condition, and who still find that they have to urinate every hour. For these patients, longer term treatment with an anticholinergic drug (muscarinic receptor antagonist) is necessary. The current drug of choice is oxybutynin, which is considered to be better than older anticholinergic treatments such as methantheline and propantheline.

The compounds of the present invention are potent antimuscarinic agents having a prolonged duration of action.

SUMMARY OF THE INVENTION

This invention relates to compounds of the formula:

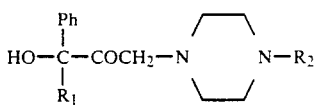

in which $R_1$ is a $C_1$ to $C_{12}$ alkyl, a substituted $C_1$ to $C_{12}$ alkyl wherein the substituent is a piperidine, pyrrolidine, morpholine, thiomorpholine or $C_3$ to $C_7$ cycloalkyl group said $C_1$ to $C_{12}$ groups being straight or branched chain, saturated or unsaturated, a $C_3$ to $C_9$ cycloalkyl, a $C_4$ to $C_9$ cycloalkyl substituted with a lower alkyl, a polycycloalkyl of 2 to 3 rings having 7 to 12 carbons;

$R_2$ is hydrogen, phenyl or phenyl singly or multiply substituted (preferably singly or doubly substituted) with halogen hydroxy, nitro, methylene dioxy, lower alkoxy lower alkyl, or trifluoromethyl, lower alkyl which may be branched chain or straight, saturated, unsaturated, or cyclic and may be optionally substituted with hydroxy lower alkoxy or acetoxyalkyl wherein the alkyl group has 1 to 3 carbons, thienyl, pyrrolyl, pyridyl, furanyl, phenyl or phenyl singly or multiply substituted (preferably singly or doubly) with halogen, hydroxy, lower alkoxy, lower alkyl, nitro, methylene dioxy or trifluoromethyl; and Ph is phenyl or phenyl para-substituted by halogen, lower alkyl lower alkoxy or trifluoromethyl.

As used herein, lower alkyl and lower alkoxy refer to groups having 1 to 6 carbons. The invention also relates to the pharmaceutically acceptable salts of the foregoing compounds, to pharmaceutical compositions containing effective amounts of such compounds and to their use in the treatment of bladder disorders.

DETAILED DESCRIPTION OF THE INVENTION

The invention is directed to 1-aryl-1-hydroxy-1-substituted-3-(4-substituted-1-piperazinyl)-2-propanones of the formula set forth above. Preferred compounds of the invention are those in which $R_1$ is cycloalkyl of 3 to 6 carbons, most preferably cyclohexyl or cyclobutyl; $R_2$ is lower alkyl. benzyl para-substituted benzyl or cinnamyl, most preferably benzyl and Ph is phenyl or para-fluorophenyl. The most preferred compound is 1-cyclobutyl-1-hydroxy-1-phenyl-3-(4-benzyl-1-piperazinyl)-2-propanone. Other preferred compounds include those in which Ph is phenyl and (i) $R_1$ is cyclohexyl and $R_2$ is methyl or (ii) $R_1$ is cyclobutyl and $R_2$ is 4-chlorobenzyl, 4-methylbenzyl or cinnamyl.

Salts of the compounds of the invention include the acid salts such as the hydrochloride, sulfate, phosphate, nitrate methanesulfonate and tartrate salts. Other pharmaceutically acceptable salts are also included in the invention, as are the various possible hydrates of each of the compounds. As will be understood by those skilled in the art, compounds of this invention may be present as d or l optical isomers as well as racemic mixtures thereof. Further, some of the compounds in which $R_1$ is a substituted cycloalkyl or a polycycloalkyl may be present as diastereoisomers which may be resolved into optical isomers. Resolution of optical isomers may be accomplished by fractional crystallization of their salts with optically active acids such as, for example, tartaric camphor-10-sulfonic, O,O-dibenzoyltartaric O,O-di(p-toluoyl) tartaric, menthyloxyacetic, camphoric, or 2-pyrrolidone-5-carboxylic acids or N-acetyltryptophane from appropriate solvents. They may also be prepared by stereoselective synthesis or by chromatographic techniques using chiral substrates or derivatives. Unless otherwise specified in the claims, it is intended to include all isomers, whether separated or mixtures thereof.

The compounds of the invention may be administered in a variety of pharmaceutical preparations well known to those skilled in the pharmaceutical art. For parenteral administration, the compounds may be prepared in aqueous injection solutions which may contain antioxidants, buffers, bacteriostats, and other additives commonly employed in such solutions. Extemporaneous injection solutions may be prepared from sterile pills, granules or tablets which may contain diluents, dispersing and surface active agents, binders, and lubricants, as well as the compound of the invention.

In the case of oral administration, fine powders or granules of the compound of the invention may be formulated with diluents and dispersing and surface active agents, and may be prepared in water, a syrup, capsules, cachets, a non-aqueous suspension or an emulsion. In dry forms, optional binders and lubricants may be present. The compositions may also include flavorants, preservatives, suspending, thickening and emulsifying agents and other pharmaceutically acceptable additives. Granules or tablets for oral administration may be coated. In general, the compositions of the invention include the compounds of the invention in a pharmaceutically effective amount in a pharmaceutically acceptable carrier.

The compounds are useful as antimuscarinic agents; more particularly, they are useful as bronchodilators, as antispasmodics, antisecretory agents, have antiulcer activity and are useful in the treatment of patients suffering from neurogenic bladder disorders. The compounds are administered in pharmaceutically effective amounts. Daily dosages will generally be at a rate of 5 to 100 mg/day, more specifically 10 to 40 mg/day. Because of their duration of action, the compounds may be administered less frequently than certain prior art antimuscarinic agents, particularly those used in the treatment of neurogenic bladder disorder.

The compounds of the invention may be manufactured by condensation of the appropriately substituted phenyl ketone derivative with lithium acetylide to give an intermediate acetylenic compound which is oxymercurated to provide a methyl ketone. This ketone is sequentially brominated and aminated with the requisite piperazine derivative. More specifically, the following synthetic route may be employed:

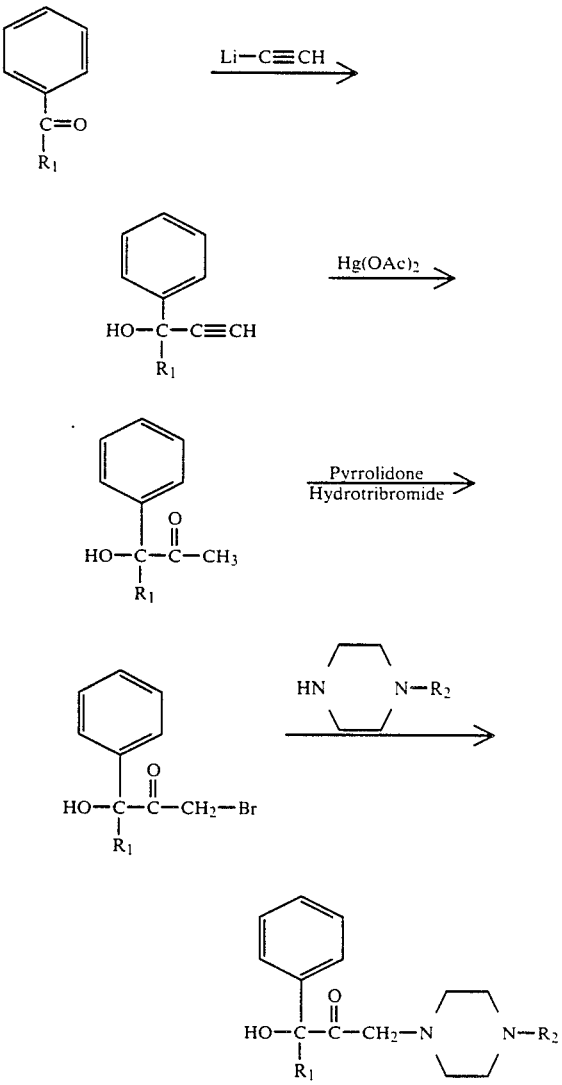

The following examples in which temperature is given in degrees Celsius and NMR signals are given in p.p.m. using $Me_4Si$ as an internal standard are illustrative of the invention.

EXAMPLE 1

1-Cyclobutyl-1-hydroxy-3-(4-phenyl-1-piperazinyl)-1-phenyl-2-propanone

In a 5-L round bottomed flask equipped with an overhead stirrer and a pressure equalizing addition funnel was placed 1460 mL (20.0 mole) of thionyl chloride. To this solution was added dropwise over a 4 hour period cyclobutanecarboxylic acid (1910 mL, 20 mole). During the addition the reaction vessel was cooled in an ice-salt bath. The mixture was stirred overnight at room temperature and then brought to reflux for 5 hours. The mixture was distilled under atmospheric pressure to give 2260.2 g of cyclobutanecarbonyl chloride, bp 130°–135° C.

In a 5-L round bottomed flask equipped with an overhead stirrer and a pressure equalizing additional funnel was placed 1500 mL of benzene and 1150 g (8.65 mole) of anhydrous aluminum chloride. The reaction vessel was cooled in an ice-salt bath. To this mixture was added very carefully over a 1.5 hour period 920 g (7.7 mole) of cyclobutanecarbonyl chloride. Following the addition, the cooling bath was removed and the mixture allowed to warm to room temperature overnight and cautiously poured onto ice. The phases were separated and the aqueous layer extracted three times with ethyl acetate. The organic layers were combined washed three times with saturated sodium bicarbonate three times with water, and once with brine. The solution was dried over anhydrous magnesium sulfate and the solvent removed under reduced pressure. The residue was distilled to give 1126 g of phenyl cyclobutyl ketone, bp 97°–102° C. at 0.1 mm Hg. NMR (CDCl$_3$) 1.8–2.6 (m, 6 H), 4.0 (q, 1 H), 7.4–7.6 (m, 3 H), 7.8–8.0 (m, 2 H); IR (neat film) 2950, 1675, 1450, 1350, 1225, 960, and 700 cm$^{-1}$.

To a solution of 180.6 g (1.96 mole) of lithium acetylide ethylenediamine complex in 900 mL of dimethyl sulfoxide was added dropwise a solution of 282 5 g (1.76 mole) of cyclobutyl phenyl ketone in 250 mL of dimethyl sulfoxide. The mixture was allowed to stir overnight and then poured onto 2 kg of ice and allowed to warm to room temperature. The mixture was extracted with four 500 mL portions of ether. The organic layers were combined washed with water and dried over anhydrous magnesium sulfate. The solvent was removed under reduced pressure and the residue distilled to give 259.9 g of 1-cyclobutyl-1-hydroxy-1-phenyl-2-propyne.

To a solution of 259.9 g (1.4 mole) of 1-cyclobutyl-1-hydroxy-1-phenyl-2-propyne in 1500 mL of acetic acid and 150 mL of acetic anhydride was added 445.2 g (1.4 mole) of mercuric acetate. The mixture was stirred overnight at room temperature. The solution was diluted with 1.5 L of methylene chloride and to it was added 1.5 L of celite and 115 g of acetamide. After being stirred for 24 hours, the mixture was filtered through a pad of celite. The solid residue was washed four times with 500 mL portions of methylene chloride. The organic layers were combined, washed three times with water, three times with saturated sodium bicarbonate. The solvent was removed under reduced pressure. The residue was dissolved in 1200 mL of methanol and 102 g (1.54 mole) of potassium hydroxide was added. The mixture was brought to reflux for 2 hours and allowed to cool to room temperature. The mixture was diluted with 1500 mL of water and extracted four times with 500 mL of ether. The organic layers were combined washed three times with water, dried over anhydrous magnesium sulfate and the solvent removed under reduced pressure. The residue was distilled bulb-to-bulb to give 224.5 g of 1-cyclobutyl-1-hydroxy-1-phenyl-2-propanone, bath temperature 110° C. NMR (CDCl$_3$) 1.7–2.2 (m, 6 H), 2.0 (s, 3 H), 3.5 (m, 1 H), 4.7 (s, 1 H), 7.2–7.5 (m, 5 H); IR (neat film) 3460, 2940, 1710, 1360, 1140, 760, 700 cm$^{-1}$.

In a 5-L round bottomed flask equipped with a reflux condenser and an overhead stirrer was placed a solution of 276 3 g (1.35 mole) of 1-cyclobutyl-1-hydroxy-1-phenyl-2-propanone in 3 L of tetrahydrofuran. To this solution was added 903 g (1.82 mole) of pyrrolidone hydrotribromide. The mixture was refluxed for 24 hours and allowed to cool to room temperature. It was partitioned between 4 L of water and 4 L of ether. The organic layer was separated, washed three times with a saturated solution of sodium bicarbonate and once with brine. It was dried over anhydrous magnesium sulfate and the solvent removed. Crystallization of the residue from hexane gave 195 g of 3-bromo-1-cyclobutyl-1-hydroxy-1-phenyl-2-propanone, mp 79°–80° C. NMR (CDCl$_3$) 1.8–2.2 (m, 6 H), 3.4–3.6 (m, 1 H), 3.9–4.1 (m, 2 H), 7.2–7.7 (m, 5 H); IR (KBr) 3471, 2946, 1725, 627 cm$^{-1}$.

To a solution of 3.64 g (0 02 mole) of 1-phenylpiperazine in 100 mL of ether was added 5.66 g (0.02 mole) of 3-bromo-1-cyclobutyl 1-hydroxy-1-phenyl-2-propanone. After being stirred overnight at room temperature, the mixture was poured onto 100 mL of a 10% solution of sodium hydroxide in brine and extracted three times with 100 mL of ether. The organic layers were combined, washed twice with water and once with brine, dried over anhydrous magnesium sulfate and the solvent removed under reduced pressure. The residue was dissolved in 50 mL of ethanol and to this mixture was added 50 mL of a 1.0 M solution of hydrogen chloride in ether. The mixture was cooled and the resulting solid collected. It was washed with ether and dried under vacuum at 100° C. to give 3.53 g of a white powder, mp 180°–182° C.; NMR (DMSO-d$_6$) 1.5–2.2 (m, 6 H), 3.2–3.5 (m, 7 H), 3.7 (t, 2 H), 4.5–4.8 (m, 2 H), 6.8–7.5 (m, 10 H); IR (KBr) 3298, 2951, 2532, 1720, 1447, 704 cm$^{-1}$, Anal. calcd for $C_{23}H_{28}N_2O_2 \cdot 2$ HCl: C, 63.19; H, 6.91; N, 6.40. Found: C, 63.08; H, 6.93; N, 6.34.

EXAMPLE 2

1-Cyclohexyl-1-hydroxy-3-(4-methyl-1-piperazinyl)-1-phenyl-2-propanone Dihydrochloride To a solution of 368 g (3.99 mole) of lithium acetylide ethylene diamine complex in 2 L of dimethyl sulfoxide was added dropwise over 2 hours a solution of 500 g (2.66 mole) of cyclohexyl phenyl ketone in 2 L of dimethyl sulfoxide. The reaction mixture was stirred overnight at room temperature and then poured onto 2 L of water and extracted three times with 1 L portions of ether. The organic layers were combined washed three times with water, twice with 10% aqueous hydrochloric acid, once again with water and finally with brine. The mixture was dried over anhydrous magnesium sulfate and the solvent removed under reduced pressure. The residue was distilled bulb-to-bulb, bath temperature 85°–90° C. at 0.1 mm Hg to give 478.3 g of 1-cyclohexyl-1-hydroxy-1-phenyl-2-propyne.

To a solution of 204.8 g (0.95 mole) of 1-cyclohexyl-1-hydroxy-1-phenyl-2-propyne in 1500 mL of acetic acid and 150 mL of acetic anhydride was added 305 g (0.95 mole) of mercuric acetate. The reaction mixture was stirred overnight and then poured into a 3-L round bottomed flask equipped with an overhead stirrer and diluted with 1500 mL of methylene chloride. To this was added 86 g (1.18 mole) of acetamide and 1 L of celite. After being stirred overnight, the mixture was filtered through a large pad of celite. The filtrate washed three times with water twice with a 5% aqueous solution of sodium hydroxide, and once with brine. The organic layer was dried over anhydrous magnesium sulfate and the solvent removed under reduced pressure. The residue was dissolved in a solution of 76 g (1.14 mole) of potassium hydroxide in 1250 mL of methanol and heated to reflux for 4 hours; the solution was cooled and then poured onto ice. The mixture was extracted four times with methylene chloride. The organic layers were combined, washed four times with water, once with brine, dried over anhydrous magnesium sulfate and the solvent removed under reduced pressure. Distillation of the residue bulb-to-bulb, bath temperature 100° C. at 0.1 mm Hg, gave 189 g of 1- cyclohexyl-1-hydroxy-1-phenyl-2-propanone, NMR (CDCl$_3$) 1.1–1.4 (m, 6 H), 1.5–1.9 (m, 4 H), 2.1 (s, 3 H), 2.4 (m, 1 H), 4.5 (s, 1 H), 7.2–7.6 (m, 5 H); IR (neat film) 3450, 2925, 2850, 1710, 1490, 1447, 1360 cm$^{-1}$.

1-Cyclohexyl-1-hydroxy-1-phenyl-2-propanone (2.83 g, 12.2 mmole) was added to 50 mL of dry tetrahydrofuran (THF). The solution was stirred and a solution of pyrrolidone hydrotribromide (6.08 g, 12.3 mmole) in 125 mL of dry THF was added dropwise over a period of 2 hours. After being refluxed for 4 hours, the reaction mixture was cooled. Ether was added and the solution washed twice with water and dried over magnesium sulfate. Upon evaporation of the solution to dryness, an orange oil was isolated. The product was purified by flash column chromatography (silica, hexane/ethyl acetate (99:1 followed by 95:5) to afford 3-bromo-1-hydroxy-1-cyclohexyl-1-phenyl-2-propanone (1 44 g, 37.7%). NMR (CDCl$_3$) 1.0–2.0 (m, 10 H), 2.4 (m, 1 H), 3.5 (s, 1 H), 4.1 (s, 1 H), 7.2–7.6 (m, 5 H).

To a solution of 2.4 g (7.7 mmole) of 3-bromo-1-hydroxy-1-cyclohexyl-1-phenyl-2-propanone in 50 mL of ether was added 2.85 g (23.4 mmole) of 4-methylpiperazine. The solution was stirred at room temperature for 18 hours and then washed twice with brine, dried over anhydrous sodium sulfate and the solvent removed under reduced pressure. Purification by flash column chromatography (silica, eluted with chloroform with 2% triethylamine) gave 2.38 g of an orange oil. This was converted into its hydrochloride salt in the usual manner to give 1-cyclohexyl-1-hydroxy-3-(4-methyl-1-piperazinyl)-1-phenyl-2-propanone dihydrochloride, NMR (DMSO-d$_6$) 0.9–1.9 (m, 10 H), 2.5 (s, 1 H), 2.9 (s, 3 H), 3.1–3.6 (m, 8 H), 4.4 (bs, 2 H), 4.6 (bs, 1 H), 7.2–7.6 (m, 5 H); IR (KBr) 3425, 3263, 1725, 1448 cm$^{-1}$. Anal. calcd for C$_{20}$H$_{32}$N$_2$O$_2$Cl$_2$: C, 59.55; H, 8.00; N, 6.94; Cl, 17.58. Found: C, 59.56; H, 8.04; N, 6.91; Cl, 17.68.

EXAMPLE 3

2-Hydroxy-2-phenyl-1-piperidino-4-(4-benzyl-1-piperazinyl)-3-butanone Dihydrochloride To a solution of 92 g (1.0 mole) of lithium acetylide ethylene diamine complex in 750 mL of dimethyl sulfoxide is added dropwise over two hours a solution of 175 g (0.86 mole) of 2-piperidinoacetophenone in 500 mL of dimethyl sulfoxide. The reaction mixture is stirred overnight at room temperature and then poured onto 2 L of water and extracted three times with 1 L portions of ether. The organic layers are combined, washed three times with water, twice with 10% aqueous hydrochloric acid, once again with water and finally with brine. After being dried over anhydrous magnesium sulfate, the solvent is removed under reduced pressure and the residue distilled to give 2-hydroxy-2-phenyl-1-piperidino-3-butyne.

To a solution of 114.5 g (0.5 mole) of 2-hydroxy-2-phenyl-1 piperidino-3-butyne in 500 mL of acetic acid and 50 mL of acetic anhydride is added 160 g (0.5 mole) of mercuric acetate. After being stirred overnight at room temperature, the mixture is poured into a 1-L round bottomed flask equipped with an overhead stirrer and diluted with 500 mL of methylene chloride. To this is added 86 g (1.18 mole) of acetamide and 1 L of celite. After being stirred overnight, the mixture is filtered through a large pad of celite. The filtrate is washed three times with water, twice with a 5% aqueous solution of sodium hydroxide, and once with brine. After the organic layer is dried over anhydrous magnesium sulfate, the solvent is removed under reduced pressure The residue is dissolved in a solution of 35 g (0.57 mole) of potassium hydroxide in 750 mL of methanol and heated to reflux for 4 hours; the solution is cooled and then poured onto ice. The mixture is extracted four times with methylene chloride. The organic layers are combined, washed four times with water, once with brine dried over anhydrous magnesium sulfate and the solvent removed under reduced pressure. Distillation of the residue gives 2-hydroxy-2-phenyl-1-piperidino-3-butanone.

2-Hydroxy-2-phenyl-1-piperidino-3-butanone (2.47 g, 10 mmole) is added to 50 mL of dry tetrahydrofuran (THF). The solution is stirred and a solution of pyrrolidone hydrotribromide (5 g, 10 mmole) in 100 mL of dry. THF is added dropwise over a period of 2 hours. After being refluxed for 4 hours, the reaction mixture is allowed to cool. Ether is added and the solution washed twice with water and dried over magnesium sulfate. The solvent is removed under reduced pressure and the product purified by flash column chromatography to give 4-bromo-2-hydroxy-2-phenyl 1-piperidino-3-butanone.

To a solution of 1 63 g (5 mmole) of 4-bromo-2-hydroxy-2-phenyl-1-piperidino-3-butanone in 35 mL of ether is added 1.76 g (5 mmole) of 4-benzylpiperazine. The solution is stirred at room temperature for 18 hours and then washed twice with brine dried over anhydrous sodium sulfate and the solvent removed under reduced pressure. Purification by flash column chromatography gives 2-hydroxy-2-phenyl-1-piperidino-4-(4-benzyl-1-piperazinyl)-3-butanone. This was converted into its hydrochloride salt in the usual manner.

EXAMPLE 4

Also prepared by the method of Examples 2 and 3 using the appropriate 1-substituted-3-bromo-1-hydroxy-1-phenyl-2-propanone and the appropriate substituted piperazine were:

1-Cyclobutyl-1-hydroxy-3-(4-methyl-1-piperazinyl)-1-phenyl-2-propanone Dihydrochloride, mp 191°–193° C. (recrystallized from ethanol-ether).

1-Cyclobutyl-1-hydroxy-3-(4-cyclobutyl-1-piperazinyl)-1-phenyl-2-propanone Dihydrochloride, mp 231°–233° C. (recrystallized from ethanol-ether).

1-Cyclohexyl-1-hydroxy-3-[4-(2-hydroxyethyl)-1-piperazinyl]-1-phenyl-2-propanone Dihydrochloride. mp 164°–166° C. (recrystallized from ethanol-ether).

1-Cyclobutyl-1-hydroxy-3-[4-(2-hydroxyethyl)-1-piperazinyl]-1-phenyl-2-propanone Dihydrochloride, mp 197°–199° C. (recrystallized from ethanol-ether).

1-Cyclobutyl-1-hydroxy-3-[4-(4-nitrophenyl)-1-piperazinyl]-1-phenyl-2-propanone Dihydrochloride, mp 134°–136° C. (recrystallized from ethanol).

1-Cyclobutyl-1-hydroxy-3-(4-propargyl-1-piperazinyl)-1-phenyl-2-propanone Dihydrochloride, mp 197°–199° C. (recrystallized from ethanol).

1-Cyclobutyl-1-hydroxy-3-(4-allyl-1-piperazinyl)-1-phenyl-2-propanone Dihydrochloride, mp 180°–182° C.

1-Cyclobutyl-1-hydroxy-3-(4-phenyl-1-piperazinyl)-1-phenyl-2-propanone Dihydrochloride, mp 180°–182° C.

1-Cyclobutyl-1-hydroxy-3-[4-(2-methoxyphenyl)-1-piperazinyl]-1-phenyl-2-propanone Dihydrochloride, mp 198°–200° C. (recrystallized from ethanol).

1-Cyclobutyl-1-hydroxy-3-[4-(2-ethoxyphenyl)-1-piperazinyl]-1-phenyl-2-propanone Dihydrochloride, mp 198°-200° C. (recrystallized from ethanol).

1-Cyclobutyl-1-hydroxy-1-phenyl-3-piperazinyl-2-propanone Dihydrochloride, mp 167°-169° C. (recrystallized from ethanol).

1-Cyclobutyl-1-hydroxy-3-(4-benzyl-1-piperazinyl)-1-phenyl-2-propanone Dihydrochloride, mp 214°-216° C. (recrystallized from ethanol).

1-Cyclobutyl-1-hydroxy-3-(4-benzyhydryl-1-piperazinyl)-1-phenyl-2-propanone Dihydrochloride, mp 187°-189° C. (recrystallized from ethanol).

1-Cyclobutyl-1-hydroxy-3-(4-ethyl-1-piperazinyl)-1-phenyl-2-propanone Dihydrochloride, mp 182°-184° C. (recrystallized from ethanol).

1-Cyclobutyl-1-hydroxy-3-(4-propyl-1-piperazinyl)-1-phenyl-2-propanone Dihydrochloride, mp 187°-189° C. (recrystallized from methanol).

1-Cyclobutyl-1-hydroxy-3-(4-cyclobutyl-1-piperazinyl)-1-phenyl-2-propanone Dihydrochloride, mp 189°-191° C. (recrystallized from ethanol).

1-Cyclohexyl-1-hydroxy-3-(4-benzyl-1-piperazinyl)-1-phenyl-2-propanone Dihydrochloride, mp 201°-203° C. (recrystallized from ethanol-ether).

1-Cyclobutyl-1-hydroxy-3-[4-(3-butenyl)-1-piperazinyl]-1-phenyl-2-propanone Dihydrochloride, mp 191°-193° C. (recrystallized from methanol-ether).

1-Cyclobutyl-1-hydroxy-3-[4-(2-methyl-2-propenyl)-1-piperazinyl]1-phenyl-2-propanone Dihydrochloride, mp 193°-195° C. (recrystallized from methanol-ether).

1-Cyclobutyl-1-hydroxy-3-[4-(3-methyl-2-butenyl)-1-piperazinyl]-1-phenyl-2-propanone Dihydrochloride, mp 191°-193° C. (recrystallized from methanol-ether).

1-Cyclobutyl-1-hydroxy-3-[4-(4-chlorobenzyl)-]1-piperazinyl]-1-phenyl-2-propanone Dihydrochloride, mp 220°-222° C. (recrystallized from ethanol-ether).

1-Cyclobutyl-1-hydroxy-3-[4-(4-methylbenzyl)-]1-piperazinyl]-1-phenyl-2-propanone Dihydrochloride, mp 208°-210° C. (recrystallized from ethanol-ether).

1-Cyclobutyl-1-hydroxy-3-[4-(4-nitrobenzyl)-1-piperazinyl]-1-phenyl-2-propanone Dihydrochloride, mp 211°-213° C. (recrystallized from methanol-ether).

1-Cyclohexyl-1-hydroxy-3-(4-allyl-1-piperazinyl)-1-phenyl-2-propanone Dihydrochloride, mp 191°-192° C. (recrystallized from ethanol-ether).

1-Cyclobutyl-1-hydroxy-3-(4-cinnamyl-1-piperazinyl)-1-phenyl-2-propanone Dihydrochloride, mp 210°-212° C. (recrystallized from methanol).

1-Cyclobutyl-1-hydroxy-3-(4-methyl-1-piperazinyl)-1-phenyl-2-propanone Dihydrochloride, mp 191°-193° C. (recrystallized from ethanol).

1-Cyclobutyl-1-hydroxy-3-(4-furfuryl-1-piperazinyl)-1-phenyl-2-propanone Dihydrochloride, mp 181°-183° C. (recrystallized from ethanol-ether).

1-Cyclohexyl-1-hydroxy-3-(4-propargyl-1-piperazinyl)-1-phenyl-2-propanone Dihydrochloride, mp 198°-200° C. (recrystallized from ethanol-ether).

1-Cyclobutyl-1-hydroxy-3[4-(3,4-methylenedioxybenzyl)-1-piperazinyl]-1-phenyl-2-propanone Dihydrochloride, mp 208°-209° C. (recrystallized from ethanol-ether).

1-Cyclobutyl-1-hydroxy-3-[4-(2-thienylmethyl)-1-piperazinyl]-1-phenyl-2-propanone Dihydrochloride, mp 196°-198° C. (recrystallized from ethanol-ether).

EXAMPLE 5

The compounds of the invention were tested to determine their antimuscarinic activity. Both the ability to induce contraction of isolated guinea pig bladder detrusor muscle strips and efficacy in the guinea pig cystometrogram test were determined.

Antimuscarinic Protocol

PURPOSE

This protocol is designed to identify compounds that possess antagonist activity at postsynaptic muscarinic cholinergic receptors on intestinal (ileal) longitudinal smooth muscle and bladder detrusor muscle.

Preparation of Bladder for Testing

Male albino guinea pigs are killed by decapitation or cervical dislocation. The peritoneal cavity is opened and the bladder is held lightly at its apex, stretched gently, and fat is lifted with fine forceps and dissected away in situ with blunt-tipped scissors as close to the surface of the bladder as possible. The tissue is placed in a latex-bottomed Petri dish that contains a modified Krebs solution (133 mM NaCl, 1.3 mM $NaH_3PO_4$, 16.3 mM $NaHCO_3$, 4.7 mM KCl, 0.6 mM $MgSO_4 \cdot 7H_2O$, 2.5 mM $CaCl_2 \cdot 2H_2O$, 7.7 mM dextrose) and cut above the neck. The bladder is collapsed into a flat pouch, which is opened by two lateral incisions and unfolded to give a rectangular sheet of tissue approximately 2 cm long and 1 cm wide. The sheet is gently stretched and pinned to the bottom of the Petri dish. Blunt separation of the mucosa, which is visible as a looser superficial pink layer is started at one end by carefully inserting the blades of micro dissecting scissors between the mucosa and muscle layers, and using gentle spreading of the blades, together with steady traction with forceps to tease the two layers apart. Clean removal of the mucosa is usually possible without any fraying or tearing of the underlying muscle. The removal of the mucosa is considered essential for improving oxygen supply to the preparation and for providing better access on both sides of the thin muscle sheet for administered drugs (Ambache and Zar, J. Physiol 210:671, 1970). The sheet is trimmed, if necessary, and cut longitudinally into four strips.

The strips are tied off with 5-0 silk suture and are then suspended in 10 mL water-jacketed glass tissue baths containing the Krebs solution maintained at 35° C. and bubbled with 95% $O_2$/5% $CO_2$. The suture connects each tissue to a isometric force-displacement transducer (Grass or Gould) coupled to a physiograph. Each preparation is suspended under a resting tension of 0.5 g and allowed to equilibrate for 36 minutes. During this period, the baths are emptied and filled every 12 minutes with 10 mL warm Krebs buffer. At the end of this period, each muscle strip is conditioned by adding 10 $\mu$M carbachol to the baths. The drug remains in contact with each tissue for 1 to 2 minutes and then is removed by four rapid rinses with 10 mL warm Krebs buffer. The preparations are allowed to recover for an additional 12 minutes before being used in experiments.

Preparation of Agonist

Carbachol is dissolved in saline to produce $2 \times 10^{-2}$ M stock concentrations. Serial dilutions (1:10) in saline or water are made from the stock solution. Appropriate volumes of these solutions are added cumulatively to the 10 mL tissue baths in order to obtain the desired bath concentrations.

Preparation of Test Compounds

Compounds that are soluble in water or saline are dissolved in these solvents to produce $2 \times 10^{-2}$ or $2 \times 10^{-3}$ M stock concentrations. Small amounts of 1 N HCl or NaOH, or 95% ethanol may be added for those agents that are not soluble in water or saline alone. Serial dilutions (1:10) in saline or water are made from the stock solution. Compounds that are insoluble in aqueous solvents are dissolved in dimethyl sulfoxide (DMSO) to produce $2 \times 10^{-2}$ M stock solutions. Serial dilutions (1:10) in water are made from the stock solution. Appropriate volumes are then added to the baths in order to obtain the desired bath concentrations.

EXPERIMENTAL

Appropriate volumes of carbachol solutions are cumulatively added to the 10 mL tissue baths to increase the concentration of carbachol in the bath step-by-step without washing out after each single dose. With each concentration step, the tissue contracts isometrically. The next concentration is added only after the preceding contraction has reached a steady value. When the next concentration step does not cause a further increase in contraction, it is assumed that the maximum effect has been obtained. The tissue is then washed with four rapid rinses with 10 mL of warm Tyrodes solution and allowed to recover for 12 minutes (Van Rossum et al., Arch. Int. Pharmacodyn. 143:240. 1963 and 143:299 (963)). Antagonism of carbachol responses in the presence of antagonist are determined by repeating the cumulative addition procedure after the tissue has been exposed to the agonist for 5 minutes.

Three or four different concentrations of antagonist are studied in the same preparations. Responses are expressed relative to the maximum contraction elicited by carbachol in the absence of antagonist. The data are collected via Buxco Data Logger and analyzed by Branch Technology's software package to obtain $K_b$ values for the antagonists.

In the case of 1-cyclohexyl-1-hydroxy-1-phenyl-3-(4-methyl-1-piperazinyl)-2-propanone, a $K_b$ value of $25.9 \pm 5.3$ nM was found. Results for other test compounds are given in Table 1.

Duration of Action Studies with In Vivo Guinea Pig Cystometrogram Model

Introduction

To assess test compounds with a more intact model system, a method which more closely mimics the natural slow filling of the bladder is used. The slow-filling cystometrogram (CMG) is used clinically to evaluate urinary bladder dysfunction (Ouslander, J. et al., J. Urol. 137:68-71 (1987)).

This clinical CMG is produced by catheterizing the bladder so it may be filled, emptied and refilled with fluid while simultaneously measuring the internal bladder pressure (Pves). Since the rate of filling can alter the response of the reflex system (Coolsaet, B., Neurourol. Urodyn. 4:263-273 (1985)), a slow rate is chosen. This allows the bladder to reach maximum capacity/pressure before sensory systems initiate the normal urge and micturition reflex patterns. We use a modification of this clinical test to determine duration of action of test compounds by repeated filling of the bladder following i.v. administration of the test compound. Peak pressure above the threshold pressure is the primary measure of action which can be inhibited by the test compounds and can be used to determine potency and duration of action in this anesthetized guinea pig model.

METHODS

Animal Subjects

Female guinea pigs (350-500 g, outbred stock from Charles River Laboratories, origin: Crl: (HA)BR Hartley,raised and kept as V.A.F.) fed Ralston Purina Guinea Pig Chow #5025 and tap water ad libidem and kept in small groups (>5) at $20° \pm 1°$ C., RH 40-50%, 12 hour light/dark cycle.

Anesthesia:

Urethane (available from Sigma, #U-2500, 1.5 g/kg, i.p.) injection made as 150 mg/mL urethane in water, is given in divided doses of 80%+20% about 30 minutes apart due to potential for overdose if delivered in single dose. This maintains a stable level of anesthesia for 3 or more hours without supplements.

Animal Preparation:

After induction of anesthesia, the animals are shaved about the medial thigh area for later femoral vein exposure and injection. They are placed supine on a heated small animal board to maintain body temperature. A saline-filled urinary catheter made of PE-100 tubing with several lateral holes near the distal tip is placed into the bladder through the urethra. Care is taken to not allow any air into the system and the tip of the catheter is lubricated with a drop of mineral oil. The catheter is connected by a series of 3-way stopcocks to a pressure transducer (Statham/Gould Model P-50), a syringe pump (Harvard Model 2274) and an exit port to empty the bladder after filling. The bladder is emptied by gentle syringe suction at the opened exit port combined with gentle manipulation and pressure on the lower abdomen. It is then rinsed out with 2-3 mL of saline and emptied again. The urethral opening is sealed about the catheter with a purse-string suture (4-0 Dermalon or silk, using a ⅜-circle cutting needle e.g., P-3). The syringe pump is set to deliver normal saline at room temperature at approximately 0 4 mL/minute with the exit port closed and the transducer open to measure the intravesicular bladder pressure during the filling process. The transducer is balanced and calibrated prior to each experiment using a column of water. For most animals, a full-scale range of 0 to 5.0 kPa (equivalent to 0 to 51 cm $H_2O$) is most useful. In some cases, peak contraction pressure will exceed 5 kPa and a rapid switch to a 0 to 10 kPa scale is needed to detect the peak response. A chart recorder (Gould=Model 2400S) records Pves at a chart speed of 0.10 mm/second.

Drug Preparation

Test drugs and reference compounds are normally prepared as a solution in normal saline, acidified or made basic as needed to get the compound into solution at the desired concentration. Drugs are delivered at selected mg/kg (calculated as free base) doses i.v. in a volume of approximately 0.5 to 0.8 mL. The selection of the desired dose to test for duration of action is based on preliminary studies where dose-response data are obtained using an escalating dose series of measures on the paradigm below. Normally for an inhibition measure, the $ID_{70}-ID_{80}$ is selected so that sufficient signal depression is observed but that the signal is not obliterated or masked by the noise of the test system.

Measurement Paradigm

After "resting" the bladder empty for 5-10 minutes, the saline infusion is started. The Pves is measured as the filling occurs. For most animals, a point will be reached within 3 to 15 minutes (approximate bladder volume of 1.2 to 6 mL) where a strong contraction occurs during this first control filling maneuver. When this is recognized and the peak pressure has subsided, the bladder is emptied as noted above and a 5 minute rest period begins. The control fills are repeated with the fixed rest periods at least three times to establish a reproducible baseline control set. A useful average of the last three fills before the drug treatment is the objective of the repeated control fill maneuvers.

In some animals, a recognizable contraction response is not evident and/or the bladder appears to be not compliant (the pressure rises continuously and rapidly as volume increases). If the contraction response does not appear within 20 minutes (about 8 mL volume) or the continuously rising Pves exceeds 2.5–3 kPa, empty the bladder and begin the fixed 5 minute rest period. Nearly all animals will begin to produce typical control responses after two or three filling maneuvers.

The following measurements are taken from the chart record:

PvesB = the baseline pressure at the beginning of a fill maneuver
PvesT = the threshold pressure where the observed contraction response begins
PvesM = the absolute maximum Pves during the contraction response
PvesP = PvesM - PvesT: peak pressure above threshold pressure
Time = infusion period until PvesT is noted (volume of the bladder is then the actual delivery rate × time, ignoring any kidney output)

After the last of the desired control fills, the femoral vein is exposed and the test drug is delivered i.v. during the midpoint of the fixed 5 minute rest period. The filling maneuvers are then repeated to observe the changes of the recorded parameters over time following the test drug administration. Peak pressure above the threshold (PvesP) is used as the primary measure of inhibition of contraction strength for the duration of action of the test compounds.

Analysis: Measurements of the listed parameters are tabulated and values for control measures averaged (usually the last three control fills) and used to compare with the post-treatment results. PvesP (and any other parameter) is then transformed to percent change from control:

$$((Result/Control\ average) \times 100) - 100$$

and plotted against time since drug administration

Because each animal serves as its own control and there is normal variability between animals, this parameter is then normalized to 100% of maximum response (i.e., maximum depression) so that the maximum depression of control is now defined as 100% of the observed depression. All measures over time then relate to the maximum depression observed.

Using the normalized response, plots are obtained of this measure against time since drug administration. For each animal, the plot is examined and a linear regression line is plotted to determine the slope of recovery of the normalized parameter (slope is thus in terms of %/minute). Extreme tail points of data are deleted when appropriate, using significance of slope criteria. This selects points where the slope begins to significantly differ from zero and includes the previous point at either end of the response recovery curve as appropriate. The regression line is then recalculated Half-life of the parameter recovery is then taken without regard to the original intercept as:

$$T_{\frac{1}{2}} = 50/\text{slope (minutes)}$$

Because half-life measures are known to not be normally distributed, the geometric mean (G.M.) and the range of values are reported for each drug treatment or dose for comparison to other treatments. Ordinary tests of significance between drug treatments can then be made on either the regression parameters of the recovery curves or by using Student's t test on the values calculated for $T_{\frac{1}{2}}$. The $ID_{50}$ is the calculated dose of compound which produces 50% of the maximal inhibition PvesP contraction strength parameter.

Results: 1-Cyclohexyl-1-hydroxy-3-(4-methyl-1-piperazinyl)-1-phenyl-2-propanone was tested in this model to determine $T_{\frac{1}{2}}$ values for recovery toward control level of the PvesP contraction strength parameter. The doses selected to test for duration of action were based on the estimates of the $ID_{70}-ID_{80}$ from prior studies and relate to equipotent doses for this measured parameter. The $T_{\frac{1}{2}}$ for this compound was $216 \pm 18$ minutes. Results for other test compounds are given in Table 1.

TABLE 1

| Compound | Antimuscarinic Activity $K_b$ in nM | CMG $ED_{50}$ in minutes |
|---|---|---|
| 1-Cyclobutyl-1-hydroxy-3-(4-methyl-1-piperazinyl)-1-phenyl-2-propanone Dihydrochloride | 24.9 | 0.13 |
| 1-Cyclobutyl-1-hydroxy-3-(4-cyclobutyl-1-piperazinyl)-1-phenyl-2-propanone Dihydrochloride | 230 | 1.64 |
| 1-Cyclohexyl-1-hydroxy-3-[4-(2-hydroxyethyl)-1-piperazinyl]-1-phenyl-2-propanone Dihydrochloride | 96 | 0.84 |
| 1-Cyclobutyl-1-hydroxy-3-[4-(2-hydroxyethyl)-1-piperazinyl]-1-phenyl-2-propanone Dihydrochloride | 201 | 1.38 |
| 1-Cyclobutyl-1-hydroxy-3-[4-(4-nitrophenyl)-1-piperazinyl]-1-phenyl-2-propanone Dihydrochloride | No Effect at 1 μM | Not Done |
| 1-Cyclobutyl-1-hydroxy-3-(4-propargyl-1-piperazinyl)-1-phenyl-2-propanone Dihydrochloride | 549 | 3.96 |
| 1-Cyclobutyl-1-hydroxy-3-(4-allyl-1-piperazinyl)-1-phenyl-2-propanone Dihydrochloride | 65 | 2.68 |
| 1-Cyclobutyl-1-hydroxy-3-(4-phenyl-1-piperazinyl)-1-phenyl-2-propanone Dihydrochloride | No Effect at 1 μM | >30 |

TABLE 1-continued

| Compound | Antimuscarinic Activity $K_b$ in nM | CMG $ED_{50}$ in minutes |
|---|---|---|
| 1-Cyclobutyl-1-hydroxy-3-(4-ethoxycarbonyl-1-piperazinyl)-1-phenyl-2-propanone Hydrochloride | No Effect at 1 μM | Not Done |
| 1-Cyclobutyl-1-hydroxy-3-[4-(2-methoxyphenyl)-1-piperazinyl]-1-phenyl-2-propanone Dihydrochloride | No Effect at 1 μM | Not Done |
| 1-Cyclobutyl-1-hydroxy-3-[4-(2-ethoxyphenyl)-1-piperazinyl]-1-phenyl-2-propanone Dihydrochloride | No Effect at 1 μM | Not Done |
| 1-Cyclobutyl-1-hydroxy-1-phenyl-3-piperazinyl-2-propanone Dihydrochloride | 86 | 0.49 |
| 1-Cyclobutyl-1-hydroxy-3-(4-benzyl-1-piperazinyl)-1-phenyl-2-propanone Dihydrochloride | 17 | 0.17 |
| 1-Cyclobutyl-1-hydroxy-3-(4-benzyhydryl-1-piperazinyl)-1-phenyl-2-propanone Dihydrochloride | No Effect at 1 μM | Not Done |
| 1-Cyclobutyl-1-hydroxy-3-(4-pyrrolidino-carbonylmethyl-1-piperazinyl)-1-phenyl-2-propanone Dihydrochloride | 210 | >10 |
| 1-Cyclobutyl-1-hydroxy-3-(4-ethyl-1-piperazinyl)-1-phenyl-2-propanone Dihydrochloride | 150 | 0.87 |
| 1-Cyclobutyl-1-hydroxy-3-(4-propyl-1-piperazinyl)-1-phenyl-2-propanone Dihydrochloride | 673 | 3.02 |
| 1-Cyclobutyl-1-hydroxy-3-(4-cyclobutyl-1-piperazinyl)-1-phenyl-2-propanone Dihydrochloride | 230 | 1.64 |
| 1-Cyclohexyl-1-hydroxy-3-(4-benzyl-1-piperazinyl)-1-phenyl-2-propanone Dihydrochloride | 20 | 0.44 |
| 1-Cyclobutyl-1-hydroxy-3-[4-(3-butenyl)-1-piperazinyl]-1-phenyl-2-propanone Dihydrochloride | 35 | 3.0 |
| 1-Cyclobutyl-1-hydroxy-3-[4-(2-methyl-2-propenyl)-1-piperazinyl]-1-phenyl-2-propanone Dihydrochloride | 100 | 2.1 |
| 1-Cyclobutyl-1-hydroxy-3-[4-(3-methyl-2-butenyl)-1-piperazinyl]-1-phenyl-2-propanone Dihydrochloride | 19 | 0.49 |
| 1-Cyclobutyl-1-hydroxy-3-[4-(4-chlorobenzyl)-1-piperazinyl]-1-phenyl-2-propanone Dihydrochloride | 16 | 2.1 |
| 1-Cyclobutyl-1-hydroxy-3-[4-(4-methylbenzyl)-1-piperazinyl]-1-phenyl-2-propanone Dihydrochloride | 9.1 | 0.38 |
| 1-Cyclobutyl-1-hydroxy-3-[4-(4-nitrobenzyl)-1-piperazinyl]-1-phenyl-2-propanone Dihydrochloride | 83 | 4.63 |
| 1-Cyclohexyl-1-hydroxy-3-(4-allyl-1-piperazinyl)-1-phenyl-2-propanone Dihydrochloride | 26 | 2.88 |

What is claimed:

1. A compound of the formula:

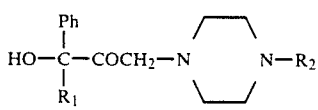

in which $R_1$ is a $C_1$ to $C_{12}$ alkyl, said alkyl being straight or branched chain, saturated or unsaturated, monosubstituted or unsubstituted, said substituents being selected from piperidine, pyrrolidine, morpholine, thiomorpholine or cycloalkyl of 3 to 7 carbons, a cycloalkyl of 3 to 9 carbons, a cycloalkyl of 4 to 9 carbons having a lower alkyl substituent or a polycycloalkyl of 2 to 3 rings having 7 to 12 carbons;

$R_2$ is hydrogen, phenyl or phenyl singly or multiply substituted with halogen, hydroxy, lower alkoxy, lower alkyl, nitro, methylene dioxy or trifluoromethyl, lower alkyl, said alkyl being branched chain or straight, saturated, unsaturated, or cyclic and substituted or unsubstituted, said substituents being selected from thienyl, pyrrolyl pyridyl, furanyl, hydroxy, lower alkoxy or acetoxyalkyl wherein the alkyl group has 1 to 3 carbons, phenyl, phenyl substituted with halogen, hydroxy, lower alkoxy, lower alkyl, nitro, methylene dioxy or trifluoromethyl; and Ph is phenyl or phenyl para' substituted by halogen lower alkyl, lower alkoxy or trifluoromethyl;

or the pharmaceutically acceptable acid salts thereof.

2. The compound of claim 1 wherein $R_1$ is a cycloalkyl of 3 to 6 carbons, $R_2$ is lower alkyl, benzyl, substituted benzyl or cinnamyl, and Ph is phenyl or para-fluorophenyl.

3. The compound of claim 1 wherein $R_1$ is a cyclohexyl or cyclobutyl Ph is phenyl and $R_2$ is methyl, benzyl or para-substituted benzyl.

4. The compound of claim 1 wherein Ph is phenyl $R_1$ is cyclohexyl and $R_2$ is methyl.

5. The compound of claim 1 wherein Ph is phenyl, $R_1$ is cyclobutyl and $R_2$ is benzyl.

6. The compound of claim 1 wherein Ph is phenyl, $R_1$ is cyclobutyl and $R_2$ is 4-chlorobenzyl.

7. The compound of claim 1 wherein Ph is phenyl, $R_1$ is cyclobutyl and $R_2$ is 4-methylbenzyl.

8. The compound of claim 1 wherein Ph is phenyl, $R_1$ is cyclobutyl and $R_2$ is cinnamyl.

9. A pharmaceutical composition for the treatment of neurogenic bladder disorder comprising a pharmaceutically effective amount of a compound of claim 1 and a pharmaceutically acceptable carrier therefor.

10. A pharmaceutical composition for the treatment of neurogenic bladder disorder comprising a pharmaceutically effective amount of a compound of claim 5 and a pharmaceutically acceptable carrier therefor.

11. A method for treating neurogenic bladder disorder comprising administering to a host an effective amount of the compound of claim 1.

12. A method for treating neurogenic bladder disorder comprising administering to a host an effective amount of the compound of claim 5.

* * * * *